United States Patent

Kroenke

[11] 4,406,837
[45] Sep. 27, 1983

[54] METHYLTRICAPRYL AMMONIUM MOLYBDATES

[75] Inventor: William J. Kroenke, Brecksville, Ohio

[73] Assignee: The B. F. Goodrich Company, Akron, Ohio

[21] Appl. No.: 402,479

[22] Filed: Jul. 28, 1982

[51] Int. Cl.$^3$ .............................................. C07F 11/00
[52] U.S. Cl. .................................................. 260/429 R
[58] Field of Search ..................................... 260/429 R

[56] References Cited

U.S. PATENT DOCUMENTS

| | | | |
|---|---|---|---|
| 3,223,625 | 12/1965 | Cuphers et al. | 260/429 R X |
| 3,290,245 | 12/1966 | Elliott et al. | 260/429 R X |
| 3,349,108 | 10/1967 | Marzluff | 260/429 R |
| 4,053,455 | 10/1977 | Kroenke | 260/429 R X |
| 4,153,792 | 5/1979 | Kroenke | 260/429 R X |
| 4,217,292 | 8/1980 | Kroenke | 260/429 R |
| 4,234,474 | 11/1980 | Kroenke | 260/429 R |
| 4,235,770 | 11/1980 | Kroenke | 260/429 R X |
| 4,247,451 | 1/1981 | Kroenke | 260/429 R X |
| 4,248,767 | 2/1981 | Kroenke | 260/429 R |
| 4,248,767 | 2/1981 | Kroenke | 260/429 R |

*Primary Examiner*—Helen M. S. Sneed
*Attorney, Agent, or Firm*—James Robert Lindsay

[57] ABSTRACT

Methyltricaprylammonium molybdates having the empirical formula $$[CH_3(C_8H_{17})_3N]_a Mo_b O_c H_d$$

where a, b and c are (2,1,4); (2,2,7); (3,5,17); (2,6,19); (4,8,26) or (6,7,24) and d is 0 or 1 are disclosed as novel amine molybdates which are useful as smoke retardant additives for vinyl chloride polymer compositions.

6 Claims, No Drawings

METHYLTRICAPRYL AMMONIUM MOLYBDATES

BACKGROUND OF THE INVENTION

Amine molybdates may be produced by reacting an amine or an amine salt with a molybdenum compound such as molybdenum trioxide ($MoO_3$), molybdic acid or a molybdenum salt in an acidic aqueous medium made acidic through the addition of a suitable acid such as an inorganic acid (exemplified by hydrochloric acid, nitric acid or sulfuric acid) or an organic acid containing 1 to 12 carbon atoms (exemplified by acetic acid, propionic acid, benzoic acid, and the like). The acidic mixture is refluxed, preferably while being stirred continuously, until the reaction is complete, usually for about ¼ to 4 hours.

Amine molybdates also may be produced, as described in U.S. Pat. No. 4,217,292, by reacting essentially stoichiometric quantities of molybdenum trioxide with an amine or an amine salt in an aqueous medium essentially free of acid and in which a water-soluble ammonium or monovalent metal or divalent metal or trivalent rare earth metal salt of an inorganic or organic acid is dissolved. Sometimes the reaction is carried out in a polar organic solvent instead of water.

The particular amine molybdate formed may depend upon which process is used to form the amine molybdate and the quantity of reactants present in the reaction mixture, as well as the reaction conditions.

SUMMARY OF THE INVENTION

The present invention pertains to a class of novel molybdates, namely, methyltricaprylammonium molybdates which may be represented by the formula:

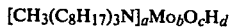

where a, b and c are (2,2,7); (3,5,17); (2,6,19); (4,8,26) or (6,7,24) and d is 0 or 1. Like many other amine molybdates, the methyltricaprylammonium molybdates function as effective smoke retardant additives for vinyl chloride polymers.

DETAILED DESCRIPTION OF THE INVENTION

Methyltricaprylammonium molybdates may be produced by reacting ammonium dimolybdate [$(NH_4)_2Mo_2O_7$] and methyltricaprylammonium chloride, [$CH_3(C_8H_{17})_3NCl$], (Aliquat 336 manufactured by Henkel Corporation) in an acidic aqueous medium. (Since Aliquat 336 consists mainly of a mixture of about 60% $C_8$ and 30% $C_{10}$ hydrocarbon chains, the "capryl" group herein is represented as $C_8H_{17}$.) Suitable acids include inorganic acids, such as hydrochloric acid, nitric acid, sulfuric acid, and the like, or mixtures thereof. The amount of acid used may be varied widely from about ½ to 10 or more molar equivalents of acid per molar equivalent of ammonium dimolybdate. However, about a 1/1 molar equivalent ratio is preferred. Sufficient water is included in the reaction mixture to insure a reaction medium that has a consistency that enables it to be easily stirred. The reaction mixture is heated to reflux while being stirred. The reaction materials are refluxed while being stirred continuously for about 0.25 to 16 hours, preferably at a temperature between 75° to 110° C. After the reaction is completed, the methyltricaprylammonium molybdate reaction product is separated from the aqueous phase by filtration or other separation procedure. The methyltricaprylammonium molybdate is washed with water and dried. The molar ratio of ammonium dimolybdate to methyltricaprylammonium chloride will influence the methyltricaprylammonium molybdates formed as a result of the reaction. Theoretical molybdenum methyltricaprylammonium chloride molar ratios from 0.5/1 to 3/1 are used. However, the actual molar ratios that can be used in the reaction can be outside the stated range, but generally will produce mixtures of the molybdates. Not all of the realizable methyltricaprlammonium molybdates can be prepared as described above. Some of them can be best prepared by reacting previously formed methyltricaprylammonium molybdates with either a strong inorganic acid, such as hydrochloric acid, or methyltricaprylammonium hydroxide in polar solvents, such as water, methanol and acetonitrile. The methyltricaprylammonium molybdates within the scope of the present invention are methyltricaprylammonium monomolybdate [$CH_3(C_8H_{17})_3N]_2MoO_4$, methyltricaprylammonium dimolybdate [$CH_3(C_8H_{17})_3N]_2Mo_2O_7$, methyltricaprylammonium pentamolybdate [$CH_3(C_8H_{17})_3N]_3 Mo_5O_{17}H$, methyltricaprylammonium hexamolybdate [$CH_3(C_8H_{17})_3N]_2Mo_6O_{19}$, methyltricaprylammonium heptamolybdate [$CH_3(C_8H_{17})_3N]_6Mo_7O_{24}$, and methyltricaprylammonium octamolybdate [$CH_3(C_7H_{17})_3N]_4Mo_8O_{26}$.

The following examples more fully illustrate the preparation of the novel methyltricaprylammonium molybdates of the present invention.

EXAMPLE I 20.00 grams of methyltricaprylammonium chloride (Aliquat 336) were added to a 1000 milliliter round-bottom flask equipped with a water-cooled condenser and a mechanical stirrer. 200 milliliters of water then were added to the flask. 3.92 grams of a 37 percent hydrochloric acid solution were mixed with 200 milliliters of water and the resulting solution was added to the flask. The contents of the flask were brought to reflux. 13.92 grams of ammonium dimolybdate were added to 100 milliliters of water and heated while being stirred to about 50° C. and then added to the flask. The mixture in the flask was heated to reflux and refluxed while being stirred continuously for 1 hour. The contents of the flask were cooled to room temperature (about 25° C.) in an ice bath and then were poured through a Buchner funnel. The light green solid reaction product collected on the filter paper was washed three times with approximately 25 milliliters of water and then was dried in a vacuum oven for 1 hour 45 minutes at 65° C. The light green waxy solid was identified by infrared analysis to be methyltricaprylammonium beta-octamolybdate.

EXAMPLE II 20.00 grams of methyltricaprylammonium chloride (Aliquat 336) were added to a 1000 milliliter round-bottom flask equipped with a water-cooled condenser and a mechanical stirrer. 200 milliliters of methanol then were added to the flask and stirring of the contents began. 13.92 grams of ammonium dimolybdate then were added to the flask along with 100 additional milliliters of methanol. 4.04 grams of a 37 percent hydrochloric acid solution were dissolved in 200 milliliters of methanol and were added to the flask. The contents of the flask were brought to reflux and refluxed while being stirred continuously for 1 hour. The liquid contents of the flask were poured through a Buchner funnel. A light green-yellow participate was collected on the filter paper. The participate was washed three times with about 25 milliliters of methanol and was dried in a vacuum oven for 2 hours 45 minutes at about 35° C. The light green-yellow reaction product was identified by infrared analysis to be methyltricaprylammonium hexamolybdate.

EXAMPLE III 1.51 grams of molybdenum oxide and 20 milliliters of a 1.0 molar solution of methyltricaprylammonium hydroxide in methanol were added to a 100 milliliter Erlenmeyer flask and stirred until the molybdenum oxide dissolved. The contents of the flask were filtered and the filtrate was rotoevaporated to dryness. A light tan oily product was obtained. Infrared analysis identified the product as methyltricaprylammonium monomolybdate.

EXAMPLE IV 10.63 grams of methyltricaprylammonium octamolybdate, 80 milliliters of acetonitrile and 16 milliliters of a 1.0 molar solution of methyltricaprylammonium hydroxide in methanol were added to a 100 milliliter Erlenmeyer flask and stirred overnight (approximately 16 hours). The contents of the flask were rotoevaporated to dryness. A light brown oily product was obtained. The product was washed with ethyl ether. The ether layer was decanted from the oily layer. The oily layer was dried to dryness on a rotoevaporator. Infrared analysis of the light brown oily product identified the product to be methyltricaprylammonium dimolybdate.

EXAMPLE V 2.60 grams of methyltricaprylammonium dimolybdate and 50 milliliters of water were added to a 125 milliliter Erlenmeyer flask. 0.20 gram of a 37 percent hydrochloric acid solution was mixed with 50 milliliters of water and added to the flask. The contents of the flask were stirred for 5 minutes. 20 milliliters of methylene chloride were added to the flask and stirred with the contents of the flask. The methylene chloride layer was separated from the aqueous layer and rotoevaporated to dryness. A cream-colored wax-like product was obtained. Infrared analysis identified the light-colored product to be methyltricaprylammonium pentamolybdate.

The methyltricaprylammonium molybdates have been found to be a smoke retardant additive for vinyl chloride polymer compositions. When used as a smoke retardant additive, the methyltricaprylammonium molybdates desirably are dissolved in an organic solvent for the molybdate (such as methylene chloride) and mixed with the dry vinyl chloride polymer particles. The methylene chloride then is allowed to evaporate from the vinyl chloride polymer leaving the methyltricaprylammonium molybdate deposited on the vinyl chloride polymer particles. Preferably, from about 0.1 to about 20 parts by weight of a methyltricaprylammonium molybdate is used per 100 parts by weight of vinyl chloride polymer.

Vinyl chloride polymers with which the methyltricaprylammonium molybdates can be used as smoke retardant additives include homopolymers, copolymers and blends of homopolymers and/or copolymers, and include chlorinated polymers thereof. The vinyl chloride polymers may contain from 0 to 50 percent by weight of at least one other olefinically unsaturated monomer. Suitable monomers include 1-olefins containing from 2 to 12 carbon atoms such as ethylene, propylene, 1-butene, isobutylene, 1-hexene, 4-methyl-1-pentene, and the like; dienes containing from 4 to 10 carbon atoms, including conjugated dienes such as butadiene, isoprene, piperylene, and the like; ethylidene norbornene and dicyclopentadiene; vinyl esters and allyl esters such as vinyl acetate, vinyl chloroacetate, vinyl propionate, vinyl laurate, alkyl acetate, and the like; vinyl aromatics such as styrene, α-methyl styrene, chlorostyrene, vinyl toluene, vinyl naphthalene, and the like; vinyl allyl ethers and ketones such as vinyl methyl ether, allyl methyl ether, vinyl isobutyl ether, vinyl n-butyl ether, vinyl chloroethyl ether, methylvinyl ketone, and the like; vinyl nitriles such as acrylonitrile, methacrylonitrile, and the like; cyanoalkyl acrylates such as α-cyanomethyl acrylate, the α-β and α-cyanopropyl acrylate, and the like; olefinically unsaturated acids and esters thereof including α,β-olefinically unsaturated acids and esters thereof such as methyl acrylate, ethyl acrylate, chloropropyl acrylate, butyl acrylate, hexyl acrylate, 2-ethylhexyl acrylate, dodecyl acrylate, octadecylacrylate, methoxyethyl acrylate, ethoxyethyl acrylate, hexylthioethyl acrylate, methyl methacrylate, ethyl methacrylate, butyl methacrylate, and the like.

The vinyl chloride polymer, in addition to the methyltricaprylammonium molybdate, may contain the usual compounding ingredients known to the art such as fillers, stabilizers, opacifiers, lubricants, processing aids, impact modifiers, plasticizers, antioxidants, and the like.

Smoke retardancy may be measured using an NBS Smoke Chamber according to procedures described in ASTM E662-79 "Test For Specific Optical Density Of Smoke Generated By Solid Materials". Maximum smoke density (Dm) is a dimensionless number and has the advantage of representing a smoke density independent of chamber volume, specimen size or photometer path length, provided a consistent dimensional system is used. Percent smoke reduction is calculated using the equation:

$$\frac{Dm/g \text{ of control} - Dm/g \text{ of sample}}{Dm/g \text{ of control}} \times 100$$

The term "Dm/g" means maximum smoke density per gram of material. Dm and other aspects of the physical optics of light transmission through smoke are discussed fully in the ASTM publication.

Smoke retardance may be measured quickly using the Goodrich Smoke-Char Test. Test samples may be prepared by dry blending polymer resin and smoke retardant additives. The blend is ground in a liquid nitrogen-cooled grinder to assure uniform dispersion of the smoke retardant additives in the resin. Small (about 0.3 g) samples of the polymer blend are pressed into pellets about ¼ inch diameter for testing. Alternatively, test samples may be prepared by blending resin, smoke retardant additives and lubricant(s) or processing aid(s) in a blender such as an Osterizer blender. The blend is milled, pressed into sheets, and cut into small (about 0.3 gram) samples for testing. The test samples are placed on a screen and burned for 60 seconds with a propane gas flame rising vertically from beneath the samples. Sample geometry at a constant weight has been found not to be significant for the small samples used in this test. A Bernz-O-Matic pencil flame burner head is used with gas pressure maintained at about 40 psig. Each sample is immersed totally and continuously in the flame. Smoke from the burning sample rises in a vertical chimney and passes through the light beam of a Model 407 Precision Wideband Photometer (Grace Electronics, Inc., Cleveland, Ohio) coupled with a photometer integrator. Smoke generation is measured as integrated area per gram of sample.

The smoke retardant property of methyltricaprylammonium molybdates is illustrated by the following examples:

EXAMPLE VI

The following recipe was used:

| Material | Parts by Wt. |
|---|---|
| Polyvinyl Chloride resin* | 100.0 |
| Lubricant** | 2.0 |
| Tin Stabilizer*** | 2.0 |
| Methyltricaprylammonium molybdate | 5.0 |

*Homopolymer of vinyl chloride having an inherent viscosity of about 0.98–1.04; ASTM classification GO-5-15543.
**A commercial polyethylene powder lubricant (Microthene 510).
***Tin Thioglycolate 5.0 grams of the methyltricaprylammonium beta-octamolybdate of Example I was milled with 100.0 grams of the polyvinyl chloride resin (in accordance with the aforesaid recipe) on a two-roll mill. The lubricant and tin stabilizer of the recipe were added to the composition on the mill. Milling was continued for about 5 minutes at a roll temperature of about 165° C. The milled composition was pressed into a 6×6×0.05 inch sheet. Pressing was done at about 160° C. for 5 minutes using 40,000 pounds (about 14,900 Kg) of force applied to a 4-inch ram. The sample (Sample 1) received a 2- minute preheat before being pressed.

5.0 grams of the methyltricaprylammonium hexamolybdate of Example II were milled with 100 grams of the polyvinyl chloride resin (in accordance with the aforesaid recipe) on a two-roll mill. The lubricant and tin stabilizer of the recipe were added to the composition on the mill. Milling was continued for about 5 minutes at a roll temperature of about 165° C. The resulting composition was pressed into a test sample (Sample 2) as described above.

The molded samples were cut into 2-7/8×2-7/8×0.50 inch sections and tested against a control sample formed utilizing the aforesaid recipe but without use of the molybdate additive. Testing was performed using the flaming mode of the NBS Smoke Chamber Test (ASTM E662-79) described hereinabove. The test results are given in Table I.

TABLE I

| Sample | Dm/g* | Smoke Reduction (%) |
|---|---|---|
| Control | 60.8 | — |
| 1 | 25.6 | 58.1 |
| 2 | 31.9 | 47.4 |

*Dm/g = maximum smoke density per gram of sample.

0.075 gram of methyltricaprylammonium monomolybdate of Example III and 1.50 grams of polyvinyl chloride resin (homopolymer of vinyl chloride having an inherent viscosity of about 0.98–1.04, ASTM classification GO-5-15543) were blended together in a nitrogen-cooled grinder. The mixture (Sample 3) was cold-pressed into ¼ inch diameter pellets weighing about 0.3 gram each.

0.075 gram of methyltricaprylammonium pentamolybdate of Example V and 1.50 grams of polyvinyl chloride resin (same type as used above) were blended together in a nitrogen-cooled grinder. The mixture (Sample 4) was formed into pellets, as described above.

A "control" sample was prepared by forming pellets of the polyvinyl chloride resin.

Testing was performed using the Goodrich Smoke-Char Test described above. The test results are set forth in Table II.

TABLE II

| Sample | Spvc* | Smoke Reduction (%) |
|---|---|---|
| Control | 65.0 | — |
| 3 | 50.2 | 22.8 |
| 4 | 53.3 | 18.0 |

*Smoke-Char Test smoke number

The improved smoke retardant vinyl chloride polymer compositions obtained by the inclusion of a methyltricaprylammonium molybdate in the composition are useful wherever smoke reduction is a desirable property, such as in carpeting, house siding, plastic components for aircraft and passenger car interiors, and the like.

I claim:

1. Methyltricaprylammonium molybdates having the empirical formula ti $[CH_3(C_8H_{17})_3N]_a Mo_b O_c H_d$ where a, b and c are (2,1,4); (2,2,7); (3,5,17); (2,6,19); (4,8,26) or (6,7,24) and d is 0 or 1.

2. The methyltricaprylammonium molybdate of claim 1 wherein a is 2, b is 1, c is 4, and d is 0.

3. The methyltricaprylammonium molybdate of claim 1 wherein a is 3, b is 5, c is 17, and d is 1.

4. The methyltricaprylammonium molybdate of claim 1 wherein a is 2, b is 6, c is 19, and d is 0.

5. The methyltricaprylammonium molybdate of claim 1 wherein a is 2, b is 2, c is 7, and d is 0.

6. The methyltricaprylammonium molybdate of claim 1 wherein a is 4, b is 8, c is 26 and d is 0.

* * * * *